United States Patent
Dicataldo et al.

(10) Patent No.: US 10,336,633 B2
(45) Date of Patent: Jul. 2, 2019

(54) MICROORGANISM SUSTENANCE IN AN ACTIVATED SLUDGE UNIT

(71) Applicant: PHILLIPS 66 COMPANY, Houston, TX (US)

(72) Inventors: Gennaro Dicataldo, Bartlesville, OK (US); Joshua D. Crow, Bartlesville, OK (US); Shana L. Bender, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 124 days.

(21) Appl. No.: 15/438,899

(22) Filed: Feb. 22, 2017

(65) Prior Publication Data

US 2017/0240445 A1 Aug. 24, 2017

Related U.S. Application Data

(60) Provisional application No. 62/298,827, filed on Feb. 23, 2016.

(51) Int. Cl.
| | | |
|---|---|---|
| *C02F 3/12* | (2006.01) | |
| *C12N 1/20* | (2006.01) | |
| *C02F 101/16* | (2006.01) | |
| *C02F 103/36* | (2006.01) | |

(52) U.S. Cl.
CPC .............. *C02F 3/12* (2013.01); *C12N 1/20* (2013.01); *C02F 2101/16* (2013.01); *C02F 2103/365* (2013.01); *C02F 2209/003* (2013.01); *C02F 2209/14* (2013.01); *C02F 2209/20* (2013.01); *Y02W 10/15* (2015.05)

(58) Field of Classification Search
CPC .. C02F 2101/16; C02F 3/12; C02F 2103/365; C02F 2209/003; C02F 2209/06; C02F 2209/14; C02F 2209/20; C02F 1/00; C02F 1/66; C02F 2101/20; C02F 2101/345; C02F 2103/08; C02F 2209/02; C02F 2209/08; C02F 2209/11; C02F 2305/06; C02F 3/04; C02F 3/102; C02F 3/103; C02F 3/108; C02F 3/1236; C02F 3/1263; C02F 3/1284; C02F 3/28; C02F 3/322; C02F 3/34; Y02W 10/15; Y02W 10/37; Y02W 10/12; C12N 1/20; Y02E 50/343

See application file for complete search history.

(56) References Cited

U.S. PATENT DOCUMENTS

| | | | | |
|---|---|---|---|---|
| 3,586,625 | A * | 6/1971 | Cole et al. | C02F 1/025 210/603 |
| 4,080,287 | A * | 3/1978 | Conway | C02F 3/085 210/150 |
| 5,958,241 | A * | 9/1999 | DeBenedetto | C02F 1/24 210/611 |
| 2009/0286295 | A1 * | 11/2009 | Medoff | C07H 3/02 435/162 |
| 2012/0168364 | A1 * | 7/2012 | Evans | C02F 1/5236 210/202 |
| 2014/0263039 | A1 * | 9/2014 | Horst | C02F 3/28 210/602 |

* cited by examiner

*Primary Examiner* — Deborah K Ware
(74) *Attorney, Agent, or Firm* — Phillips 66 Company

(57) ABSTRACT

Processes and systems for maintaining a live culture of activated sludge in the activated sludge unit of a petroleum refinery during an extended refinery shut-down. In the absence of a source of refinery wastewater, a living culture of activated sludge comprising aerobic prokaryotes and/or eukaryotes that nitrify ammonia is maintained by redirecting at least a portion of clarified wastewater leaving the clarifier portion of an activated sludge unit. The redirected clarified wastewater is mixed with an organic food source that may be ammonia and/or ethyl acetate, a source of phosphate ion, and the pH is adjusted to produce a growth media that is returned to the aeration chamber of the activated sludge unit. After a time exceeding one week, the input of refinery wastewater to the aeration chamber is resumed while discontinuing the redirecting of the clarified wastewater.

12 Claims, 5 Drawing Sheets

MICROORGANISM SUSTENANCE IN AN ACTIVATED SLUDGE UNIT

CROSS-REFERENCE TO RELATED APPLICATIONS

This application is a non-provisional application which claims the benefit of and priority to U.S. Provisional Application Ser. No. 62/298,827 filed Feb. 23, 2016, titled "Microorganism Sustenance In An Activated Sludge Unit," which is hereby incorporated by reference in its entirety.

STATEMENT REGARDING FEDERALLY SPONSORED RESEARCH OR DEVELOPMENT

None.

FIELD OF THE INVENTION

The present invention relates to processes for sustaining a microbial culture in a state suitable for immediate resumption of refinery water treatment following an extended refinery shut-down.

BACKGROUND

An extended refinery maintenance shutdown (or, "turn-around") is typically performed every 10-20 years, and can interrupt wastewater flow to Activated Sludge Units (ASU). An ASU assists in remediating refinery wastewater by removing excess nitrogen and carbon compounds. The ASU employs a broad consortium of microorganisms to remove water-soluble pollutants that are regulated under the Clean Water Act in the Unites States, and local and national regulations in other countries. These microorganisms depend on a constant influx of wastewater to provide both a food source (residual organic carbon) as well as nutrients (mainly nitrogen and phosphorus) needed for their survival.

An extended interruption in the flow of refinery wastewater leads to the death of these microorganisms and a can result in a significant delay when restarting refinery operations due to insufficient wastewater remediation capacity within the ASU.

Accordingly, a need exists for a process and system that can prevent large-scale loss of microbial flora in the ASU during an extended maintenance periods where a constant influx of refinery wastewater is not available.

BRIEF SUMMARY

In certain embodiments of the present invention, there is provided a process comprising A process for maintaining a living culture of activated sludge in an refinery activated sludge unit during an extended refinery maintenance shut down, comprising: (a) providing a refinery activated sludge unit containing a living culture of activated sludge that comprises aerobic prokaryotes, aerobic eukaryotes, or mixtures thereof that nitrify ammonia to form nitrites and nitrates, where the activated sludge unit comprises 1) an aeration chamber comprising at least one inlet that receives refinery wastewater and mixes it with the living culture to produce a treated wastewater having lower levels of at least one of ammonia, amines, and organic carbon, and 2) a clarifier that receives treated wastewater from the aeration chamber. The clarifier allows gravity settling of the living culture and produces an effluent comprising clarified wastewater that leaves the clarifier through at least one outlet;

The process further comprises: (b) discontinuing an input of refinery wastewater comprising ammonia and residual organic carbon to the at least one inlet of the aeration chamber, and redirecting the clarified wastewater leaving the clarifier to the at least one inlet of the aeration chamber, thereby recycling nutrients present within the clarified wastewater and conserving water; (c) measuring the levels of total organic carbon and ammonia in the clarified wastewater on an intermittent basis (optionally, daily), and adding sufficient acetic acid to the clarified wastewater to maintain a concentration between about 5 mM and about 20 mM, adding a source of phosphate ion sufficient to maintain a phosphate ion concentration between about 500 uM and about 1 mM, adding a source of ammonia sufficient to maintain a concentration between about 1 mM and about 2 mM and adding sufficient sodium hydroxide to maintain the pH of the clarified wastewater between about pH 7.5 and about pH 9; and (d) resuming the input of refinery wastewater through the at least one inlet of the aeration chamber after a period of time exceeding 1 week, (optionally, 2 weeks or even 4 weeks) and discontinuing the redirecting of the clarified wastewater to the aeration chamber.

In certain embodiments, the clarified wastewater is maintained with a dissolved oxygen content of at least 2 mg per liter, optionally at least 5 mg per liter.

Certain embodiments further comprise a step after part c) of intermittently removing a portion of the living culture to maintain an average living culture age of between 20 to 40 days.

Certain embodiments comprise intermittently removing of a portion of the living culture occurs daily. The intermittent removal of a portion of the living culture may reduce the suspended solids to a concentration less than 4000 mg/L, optionally less than 3000 mg/L.

In certain embodiments, the refinery wastewater is derived from at least one of refinery desalter effluent, refinery stripped sour water, refinery tank bottom draws and spent caustic.

In certain embodiments, ethyl acetate is added to the clarified wastewater instead of acetic acid and maintained a concentration between about 5 mM and about 20 mM. In other embodiments, a mixture of acetic acid and ethyl acetate is added to the clarified wastewater and maintained at concentration between about 5 mM and about 20 mM. Optionally, the pH is maintained between about pH 8 and about pH 9.

BRIEF DESCRIPTION OF THE DRAWINGS

A more complete understanding of the present invention and benefits thereof may be acquired by referring to the follow description taken in conjunction with the accompanying drawings in which.

Figure 1:
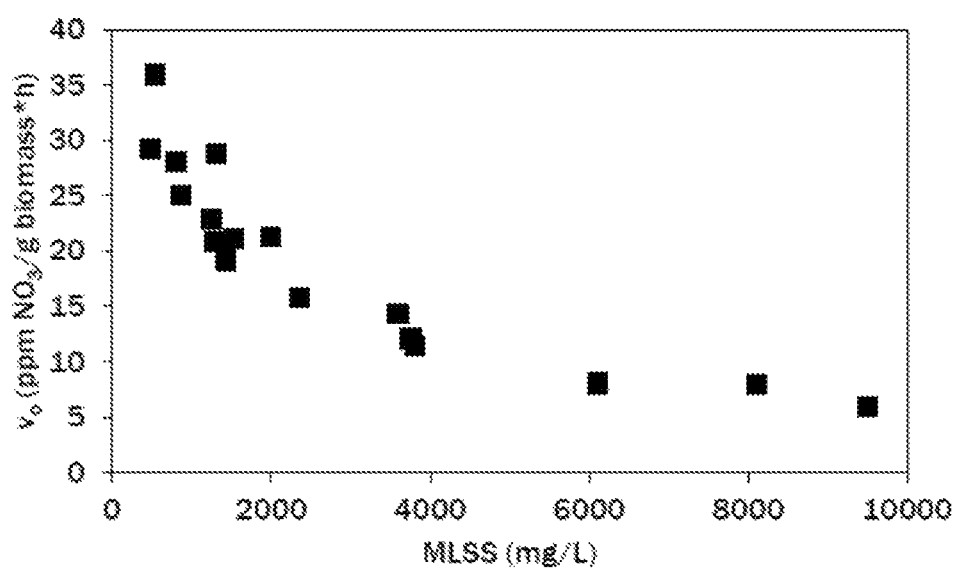
FIG. 1 is a graph depicting the rate of nitrate production in a living culture of activated sludge versus the density of mixed liquor suspended solids (MLSS) in the culture.

The invention is susceptible to various modifications and alternative forms, specific embodiments thereof are shown by way of example in the drawings. The drawings may not be to scale. It should be understood that the drawings and their accompanying detailed descriptions are not intended to limit the scope of the invention to the particular form disclosed.

DETAILED DESCRIPTION

The inventive processes and systems relate to sustaining a living culture comprising microorganisms in a Activated Sludge Unit of a commercial refinery that has been taken offline for extended maintenance.

Refinery wastewaters contain a multitude of chemicals and suspended solids and are derived from many sources of process water in the refinery, including desalter effluent, stripped sour water, tank bottom draws, and spent caustic. The effluent contaminants from those processes include organic compounds (COD), hydrocarbons, suspended solids, phenols, benzene, sulfides and ammonia, among others. Certain of these compounds have been deemed hazardous to the environment if present above a legally-defined threshold concentration. Thus, US federal laws limit the concentration of compounds such as ammonia, as well as total organic content (TOC) in water released to the environment.

Biological treatment is the most common wastewater treatment technology used to remove ammonia and dissolved organic compounds in the oil refining industry. Secondary treatment of wastewater produced during refining operations is typically performed by the activated sludge treatment process. Activated sludge is most commonly a continuous suspension of aerobic microorganisms in a wastewater containing suspended colloids, dissolved organic compounds, and inorganic materials. During treatment, wastewater is aerated in a basin containing activated sludge composed of both heterotrophic bacteria to remove organic carbon and autotrophic bacteria to remove ammonia. The most prominent process for ammonia removal is aerobic biological conversion to nitrate ($NO^{3-}$). This process is known as nitrification and is the preferred pathway for commercial refineries to meet ammonia discharge standards in wastewater. The need to oxidize ammonia during wastewater treatment arises from concerns over the effects of ammonia on receiving water with respect to dissolved oxygen (DO) concentration and toxicity to fish. Other concerns are the need to control eutrophication, or algal blooms, and the need to control nitrogen for water reuse applications The nitrification process is typically performed by activated sludge, a complex ecosystem consisting of a variety of microorganisms, both prokaryotic and eukaryotic in nature, which aggregate together to form flocs. The characteristics of the flocs are the basis for the design of the secondary water treatment units in the refineries. Without the aggregation and formation of flocs that can be separated from the wastewater by sedimentation, it would be cost-prohibitive to separate the treated water from the biomass.

In nitrification, enzymatic reactions by three different enzymes convert ammonia to nitrate. Two different species of bacteria work in coordination to convert ammonia (and organic amines) to nitrate. Microorganisms of the genus Nitrosomonas complete the first two of three reactions; converting ammonia/amines to first hydroxylamine via ammonia monooxygenase and to nitrite by hydroxylamine oxidoreductase. Nitrosomonas secretes the produced nitrite from the cell into the environment. Nitrobacter contains the enzyme nitrite oxidoreductase that catalyzes the conversion of nitrite to nitrate, completing the nitrification pathway. Although Nitrosomonas secretes nitrite as an intermediate, it is unstable and not easily detected in nitrification systems. Therefore, nitrate measurements are usually used to confer conversion and reaction rates.

The energy produced during these enzymatic reactions is utilized by both groups for survival. These reactions must be conducted on a large scale to effectively treat the large volume of wastewater produced by a commercial refinery, and are typically conducted in a large, aerated bioreactor known as an activated sludge unit (ASU). Activated sludge also includes heterotrophic microorganisms that utilize the organic carbon, amines and ammonia within refinery wastewater as a food source, thereby reducing the total organic carbon (TOC) content and ammonia content of the treated refinery water.

In certain embodiments of the inventive processes and systems, refinery wastewater is fed into a first portion of an ASU, where activated sludge is suspended in aerated refinery process water that typically contains dissolved oxygen in the amount of 2-10 ppm, preferably greater than about 5 ppm, greater than about 6 ppm, or even greater than about 7 ppm. In certain embodiments, the dissolved oxygen concentration may be held within a range, for example, in a range from about 2 to about 10 ppm, from about 5 to about 10 ppm, from about 6 to about 10 ppm, or even from about 7 to about 10 ppm.

A mixture comprising activated sludge and treated wastewater then decants to a clarifier portion of the ASU, where large agglomerations of microorganisms (known as "flocs") separate from treated wastewater by sedimentation, producing clarified wastewater. The sedimented flocs of activated sludge are recovered from the bottom of the clarifier and reused in the aeration chamber section. The clarified wastewater comprises lower levels of organic carbon and ammonia (preferably below threshold values set by government regulations) and can then be either safely released to the environment, or re-utilized by the refinery after further processing.

In certain embodiments of the system disclosed herein, the clarified wastewater is recycled to the aerating chamber via a conduit comprising at least one valve. The valve can be operated (opened) to alter the flow of clarified wastewater form being released into the environment, to instead being returned to the aeration chamber.

Because of the large mass of microorganisms needed to remove ammonia and organic carbon from the large volumes of wastewater produced by a commercial refinery, a significant amount of time is required to accumulate the quantity of culture needed to properly treat all wastewaters produced by the refinery to a level where the water can be safely released. An extended loss of wastewater influx to the ASU eliminates the food/energy source for these microorganisms and can result in the loss in most (if not all) of the culture during an extended refinery shut down that can last weeks, or even months. Once influx of refinery wastewater is restored after an extended refinery shut down, recovery of the culture often requires many weeks and necessitates that extraordinary temporary measures be taken to prevent discharge of untreated refinery water to the environment. For example, untreated wastewater that exceeds the capacity of the ASU may need to be temporarily stored in a holding pond until the living culture in the ASU recovers. It has been estimated that following a major refinery maintenance event, each week of delay in resuming refinery wastewater flow through a commercial ASU costs an additional 2.5 million dollar in lost profit.

We have empirically determined that maintaining the health and functional capability of a living microbial culture in an activated sludge unit depends upon: 1) factors that affect the biochemical processes of the microorganisms, such as the pH and temperature, 2) factors that affect microbial growth, such as concentration of organics and ammonia, and 3) the concentration of nutrients, (including phosphate) and dissolved oxygen (DO). We have determined that not only are there optimal ranges for these variables, but that maintaining the functional capability of the culture to absorb contaminants and denitrify requires that certain variables be maintained within a relatively narrow range during the time that the ASU is in recirculation mode.

In certain embodiments, the viability of the activated sludge culture depends upon maintaining an effective concentration of organic food source for heterotrophic organisms and an effective concentration of reduced nitrogen suitable to maintain levels of nitrifying bacteria that allow rapid resumption of refinery water treatment following the resumption of various refinery processes after an extended downtime. In certain embodiments, the organic food source may be acetic acid, an alkyl acetate, or any combination of these. In certain embodiments, the alkyl acetate is ethyl acetate. In certain embodiments, the acetic acid or alkyl acetate is added to the clarified wastewater (that is being recycled to the aerating chamber) to maintain a concentration in a range from about 5 mM to about 20 mM (or 25% of the acetate present during normal operation of the ASU).

A source of ammonia is also required to support the nitrifying bacteria present in the activated sludge. In certain embodiments, this source is ammonium phosphate. In certain embodiments, sufficient ammonia is added to maintain a concentration of between about 1 mM and about 2 mM. In certain embodiments, sufficient ammonia is added to match approximately 25% of the original total organic concentration of the refinery wastewater. Regardless of the source of ammonia, it must be in a form that is readily biodegradable to allow it to act as a food source and/or energy source for the nitrifying bacteria and other microorganisms.

In certain embodiments, a source of phosphate ion is also added to the clarified wastewater (that is being recycled to the aerating chamber) sufficient to maintain a phosphate ion concentration of between about 500 uM and about 1 mM. Phosphate serves as an essential nutrient for the activated sludge culture, in particular, for the aerobic heterotrophic bacteria within the sludge. In certain embodiments, the concentration of phosphate ion in the culture is maintained at a concentration that is about 20% of the concentration of ammonia.

In certain embodiments, the pH of the clarified wastewater is monitored periodically in order to assess the need to adjust the pH of the clarified wastewater. In certain embodiments, when a pH value of less than a given threshold value is detected, sufficient sodium hydroxide is added to the clarified wastewater to maintain the pH between about pH 7 and about pH 9. In certain embodiments, to maintain the pH between about pH 7.5 and about pH 9, or between about pH 7.5 and about pH 9, or even between about pH 8 and about pH 9.

The suspended solids concentration of the culture is maintained within a given range to maintain the viability of the living culture of activated sludge. The quantity of living organic matter suspended in solution is "mixed liquor suspended solids" (MLSS) and is in expressed in mg/L In certain embodiments, this value is maintained at less than 4000 mg/L. In other embodiments, this value is maintained at a value of less than 3000 mg/L. Maintaining the culture to meet these criteria for suspended solids may require intermittently removing a portion of the living culture to prevent overgrowth. In general, enough of the culture should be removed on a periodic basis to maintain the average age of the microorganisms within the culture at about 20 to about 40 days.

The carbon loading of the culture is also maintained within a range to assure the viability of the activated sludge culture during extended lack of input of fresh refinery wastewater. Carbon loading is referred to as the Food/Mass ratio (F/M) and is calculated as shown in Example 5 (below). In certain embodiments, the F/M ratio is maintained at less than 0.2, less than 0.1 or between 0.03 and 0.1. We found that F/M ratios of 0.2 or greater were highly detrimental to growth (see Example 4) of the activated sludge culture, adversely affected the sedimentation properties of flocs within the activated sludge culture, and decreased the ability to maintain nitrification within the culture.

The following examples are intended to be illustrative of specific embodiments in order to teach one of ordinary skill in the art how to make and use the invention. These examples are not intended to limit the scope of the invention to less than is defined by the appended claims.

Example 1

We developed a bench scale ASU to allow the study of growth conditions that would support a living culture within an ASU in a condition suitable to immediately resume effective treatment of refinery wastewater following an extended refinery shut down and consequent loss of refinery wastewater input to the ASU. The setup was composed of a 0.9 L glass vessel serving as aeration chamber connected to a 2 L vessel serving as a clarifier. Supernatant from the clarifier was collected as effluent. Refinery wastewater was fed to the bottom of the aeration chamber and a side-port on the vessel was used for overflow to the clarifier. Activated sludge recovered at the clarifier was returned to the aeration chamber at the mid-height point of the vessel. The aeration chamber was aerated using an air sparger stone near the bottom of the vessel and the contents were mixed using a single shaft impeller that dispersed air bubbles and kept the activated sludge in suspension. A living sample of activated sludge was obtained from a commercial refinery ASU and suspended at a concentration of 4000 mg/L.

Example 2

We conducted tests to determine whether viability of the living culture within an ASU could be maintained by supplementing recycled refinery water with any of three possible organic food sources: acetic acid, a 1:1 mixture of acetic acid and molasses, or molasses only. For all experiments, the recycled refinery wastewater was additionally supplemented with from 0.89 to 1.18 mM ammonia, and from 0.60 to 0.78 mM phosphate, with pH maintained at 7.5. Water leaving the clarifier was recycled back into the aeration chamber. 1) without additional supplementation, 2) supplemented with a mixture of 50:50 acetic acid/molasses, or 3) supplemented with molasses alone.

TABLE 1

Elimination of organics and ammonia by activated sludge in the presence of either refinery wastewater, or refinery wastewater that was recirculated into the ASU following addition of 1) 1.67 mM acetate, 2) 1 mM mixture of 50:50 acetate/molasses, or 3) 0.17 mM molasses (alone).

| Feed | COD Removal % | Ammonia Removal % | Pass or Fail |
|---|---|---|---|
| Refinery wastewater | 84% | 99% | Pass |
| Acetate | 88% | 99% | Pass |
| Acetate/Molasses (50/50) | 92% | 99% | Pass |
| Molasses | 62% | <80% | Fail |

We defined adequate ammonia removal as being above 80%. It was clear that the addition of either acetate or a mixture comprising acetate/molasses provided adequate nutrients for sustenance of the microorganisms required for nitrification of the ammonia present in the sample.

Example 3

We conducted additional tests to determine whether viability of the living culture within an ASU could be maintained by supplementing recycled refinery water with two possible organic food sources: a synthetic feed formulation 0.025 vol % acetic acid, or an alternative synthetic feed formulation comprising 1:1 mixture of 0.08 vol % acetic acid with cane sugar low sulfur molasses. Both synthetic feed formulations were also supplemented with 15-20 mg/L ammonia and phosphorus at a 5:1 ratio.

Figure 2:
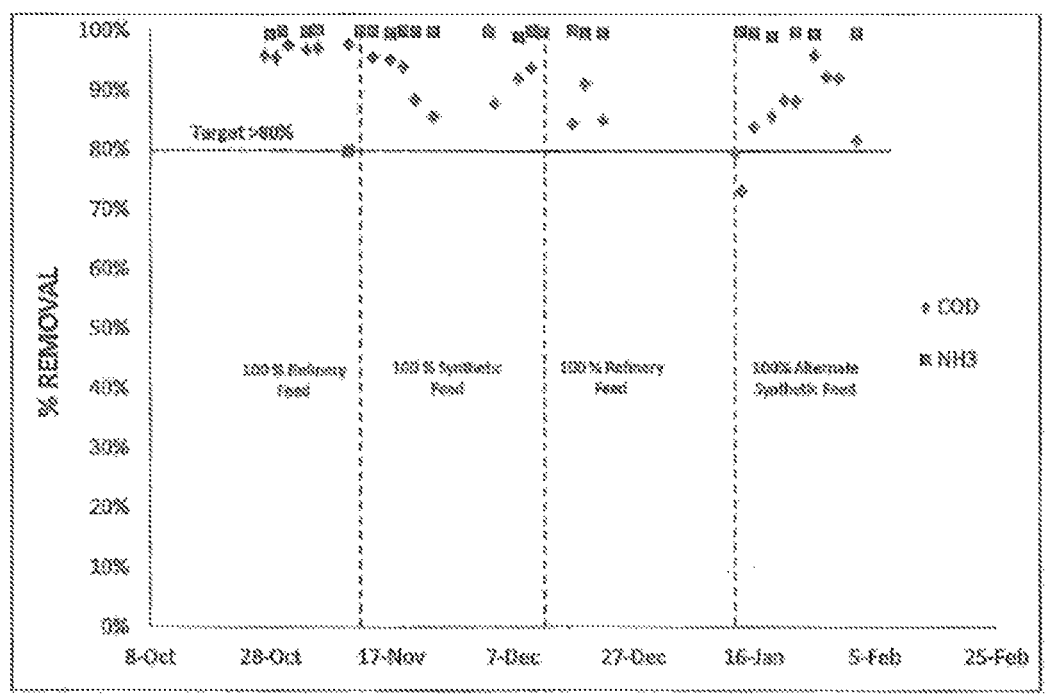
FIG. 2 is a graph depicting percent removal of carbon (COD) and ammonia (NH3) in a bench-scale Activated Sludge Unit over the course of several months.

Utilizing the bench-scale ASU apparatus described in Example 1, we monitored the conversion of both organics and ammonia over time in response to exposure to 1) refinery wastewater alone or supplemented with one of the two synthetic feed formulations (FIG. 2). The feed to the ASU was initially 100% from a refinery wastewater, then after three weeks, transitioned to 100% synthetic feed formulation for an additional three weeks. The input was then switched back to 100% refinery wastewater to simulate an extended turnaround/maintenance period during a complete refinery shut-down. Finally, the input was switched to the alternative synthetic feed for three weeks.

The performance of the ASU showed to be above the 80% target for both synthetic (100% acetic acid and nutrients) and the alternate synthetic feed (50% acetic acid, 50% molasses and nutrients). FIG. 2 indicates that each synthetic feed formulation was an adequate replacement for refinery wastewater. The target percent removal for both organics (measured by Chemical Oxygen Demand (COD)) and ammonia (NH3) was above and ammonia was set a 80% or above. This target was met or exceeded for nearly all time points through the four month duration of the experiment.

Example 4

We tested the effect of ammonia concentration on nitrification kinetics in samples of activated sludge suspended in a minimal medium comprising 1.1 mM NH4Cl, 0.1 mM KH2PO4, 0.1 mM MgSO4, 1.0 mM CaCO3, and 5.7 mM ethyl acetate at pH 7.5 shaken in a 30° C. incubator. Mixed liquor suspended solids (MLSS) concentration of the cultures was approximately 1600 mg/L.

We looked at effects of activated sludge culture concentration and the rate of nitrification in media containing 20 ppm ammonia. Nitrification proceeded quickly in the activated sludge cultures, reaching nearly 50% completion within eight hours and 90% completion within 24 h. However, above a MLSS of 2000 mg/L, a significant inhibition of nitrate production was observed (see FIG. 2) indicating an upper limit to the advisable culture density in order to preserve nitrification capability of the culture.

Example 5

To establish potential effects of dissolved oxygen on activated sludge growth and nitrification, activated sludge was incubated with refinery waste water at a mixed liquor suspended solids (MLSS) concentration of 4000 mg/L at 30° C., aerated with constant stirring. The dissolved oxygen (DO) was maintained at an average of 6.8 ppm and the temperature was kept constant at 30° C. The system reached an effective steady state in which in average 97%±7% of the ammonia was removed from the waste water.

Figure 3:
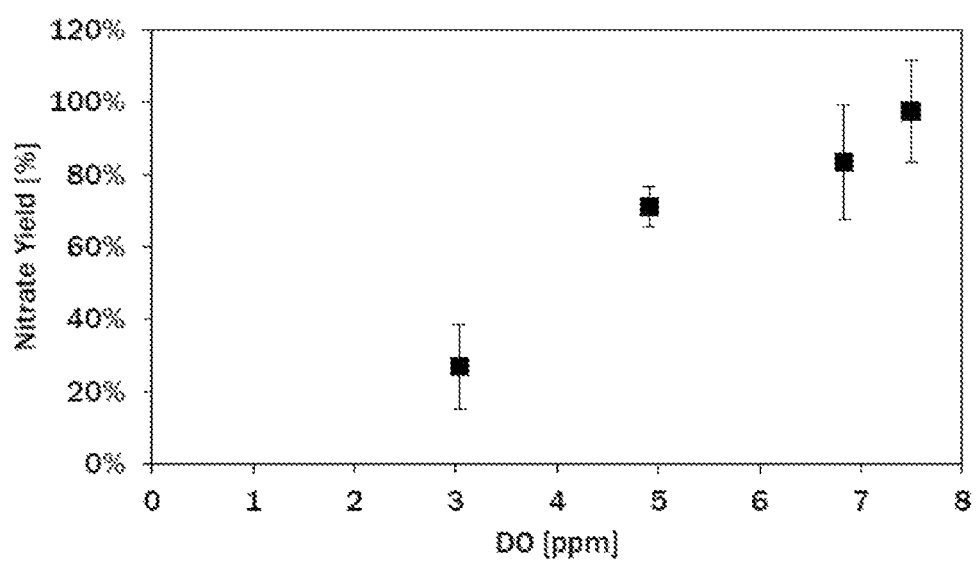
FIG. 3 is a graph depicting percent conversion of ammonia to nitrate in a living culture of activated sludge over a period of one week at various dissolved oxygen (DO) concentrations.

In order to establish the effect of oxygen on nitrification, the flow of oxygen into the ASU was next varied to adjust the dissolved oxygen to between 3 ppm and 7.5 ppm. At each set value for dissolved oxygen, the system was allowed time to stabilize. Once an effective steady-state was reached, data was collected for a week. FIG. 3 shows the effect of the dissolved oxygen on ammonia removal at the ASU. Nitrate production was found to be directly proportional to dissolved oxygen concentration with dissolved oxygen levels at or above 5 ppm showing acceptable levels of nitrate production, indicating adequate ammonia removal under such conditions. However, at a dissolved oxygen level of 3 ppm, the performance of the system decreased as a function of time and the system did not stabilize, which lead to an average nitrate yield of only 3%. These results demonstrate that nitrifying capability of the culture does not appear to be adequately supported by low concentrations of dissolved oxygen (i.e., 3 ppm or less).

Example 6

Carbon loading is known as the F/M ratio (food/mass). The formula for calculating the F/M ratio is as follows:

$$F/M\text{ratio}=[BOD\ (mg/L)*Flow(MGD)*8.34]/\text{microorganisms (lbs)}$$

The food portion of the equation is a measurement of the chemical oxygen demand (COD) (or the biological oxygen demand (BOD)) needed to remove the organic molecules from the media. The M variable reflects the amount of microorganisms in the system.

We sought to determine whether varying the F/M ratio had a significant effect on the viability of the activated sludge, and whether nitrifying bacteria would continue to nitrify under high F/M conditions. Initially, the F/M ratio was set to 0.1 by growing activated sludge samples in 50 ppm ethyl acetate. Under these conditions, the activated sludge culture converted approximately 69% of the available nitrogen to nitrate (FIG. 4, open diamonds) and microbial agglomerations (i.e., flocs) were large and irregular in shape (results not shown). Typical floc sizes were between 150-500 µm in diameter, and contained a healthy population of both prokaryotes and eukaryotes. Increasing the F/M ratio to 0.2 after one month led to a rapid, 50% decrease in nitrate formation (FIG. 4, grey circles), suggesting the increased F/M ratio rapidly inhibited the nitrifying bacteria. Increasing the F/M also led to an increase in free-floating bacteria observed on the periphery of the floc (results not shown).

Figure 4:
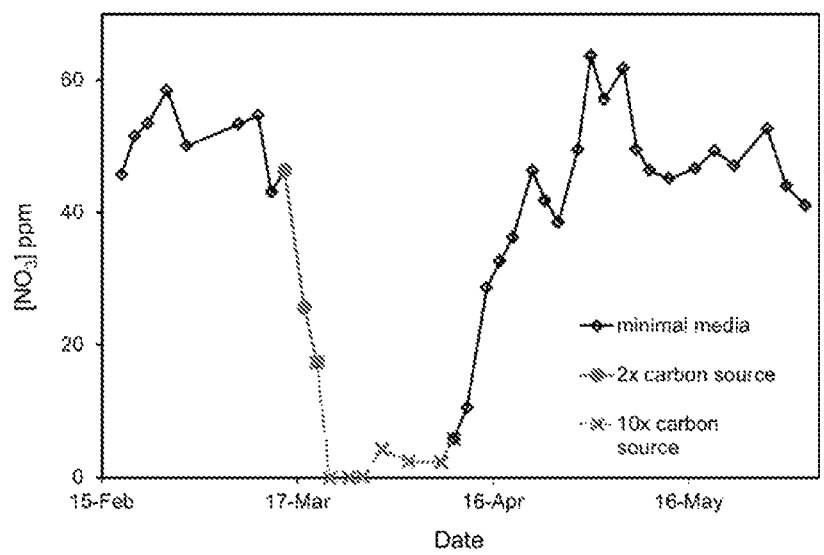
FIG. 4 is a graph depicting the concentration of nitrate (indicative of nitrate production) in a living culture of activated sludge versus the concentration of organic compounds present in the culture over time.

Further increasing the F/M ratio five-fold to a value of 1.0 caused complete inhibition of nitrification in the cultures (FIG. 4, grey Xs). Under these conditions, large quantities of filaments and free-floating bacteria were observed (results not shown). We believe that this inhibition of the nitrification process was at least partly due to increased growth of heterotrophs in the culture, which depleted the levels of dissolved oxygen required for nitrification by the nitrifying bacteria.

Nitrification recovered over the course of two weeks when F/M ratio was returned to 0.1 (FIG. 4, open diamonds on right). Once again, the activated sludge culture returned to forming large flocs suitable for proper sedimentation of the culture in the clarifier of an ASU. At higher levels of ethyl acetate, the biodiversity had shifted towards filaments, fungi, and single-celled bacteria with no activated sludge flocs. This led to a loss of nitrifying bacteria, and consequently, nitrate production. Additionally, large amounts of free cells found gave the activated sludge culture a milky appearance and the lack of large agglomerated flocs prevented proper sedimentation in the ASU.

Example 7

Figure 5:
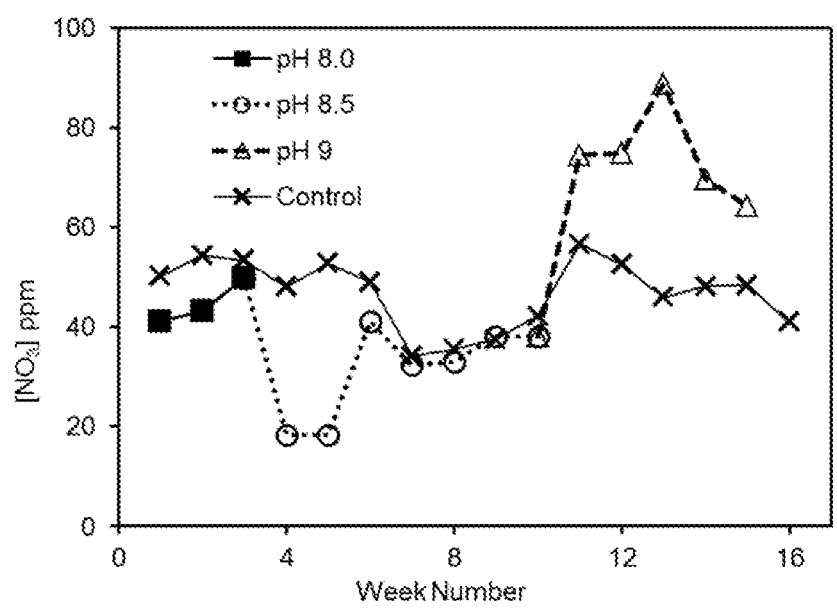
FIG. 5 is a graph depicting the concentration of nitrate (indicative of nitrate production) in a living culture of activated sludge versus the pH of the culture over a period of 16 weeks.

We varied the pH of activated sludge cultures between pH 7.5-9 to determine any effects of increasing pH on nitrification efficiency. FIG. 5 shows the production of nitrate as measured weekly over the course of the 16 week experiments. Control cultures were maintained at pH 8 (FIG. 4, black X). At pH 8.5, the culture adapted in approximately three weeks, indicating a long-term physiological transition. The pH was later increased to pH 9 in certain samples (FIG. 5, open triangles), which significantly increased the production of nitrate compared to the control cultures.

We believe that this high nitrate production rate was likely associated with the pKa of ammonia (pKa=9.25). As the prevalence of ammonium ion decreased with increasing pH, the ability of the culture to produce nitrate increased, suggesting that the non-protonated form of ammonia may be more easily transported into the nitrifying bacteria. Uncharged molecules traverse cellular membranes without requiring active transport, while transport of their charged counterparts is limited by the use of a protein-mediated transport system. These results suggest that increased nitrate production may be achieved by maintaining activated sludge at basic pH, and above pH 8.5 if possible.

In closing, it should be noted that each and every claim listed below is hereby incorporated into this detailed description as an additional embodiment of the present invention. Although the systems and processes described herein have been described in detail, it should be understood that various changes, substitutions, and alterations can be made without departing from the spirit and scope of the invention as defined by the following claims. It is not intended that the scope of the invention be limited to the disclosed embodiments set forth in the examples. Rather, the appended claims should be given the broadest interpretation consistent with the description as a whole.

We claim:

1. A process for maintaining a living culture of activated sludge in a refinery activated sludge unit during an extended refinery maintenance shut down, comprising:
    (a) providing a refinery activated sludge unit containing a living culture of activated sludge,
        wherein the activated sludge comprises aerobic prokaryotes, aerobic eukaryotes, or mixtures thereof that nitrify ammonia to form nitrites and nitrates,
        wherein the activated sludge unit comprises an aeration chamber comprising at least one inlet that receives an input of refinery wastewater comprising ammonia and residual organic carbon and mixes the refinery wastewater with the activated sludge to produce a treated wastewater characterized by lower levels of at least one of ammonia, amines, and organic carbon,
        wherein the activated sludge unit further comprises a clarifier that receives the treated wastewater from the aeration chamber and separates out agglomerations comprising activated sludge by sedimentation, thereby and producing an effluent comprising clarified wastewater that leaves the clarifier through at least one outlet;
    (b) discontinuing the input of refinery wastewater to the aeration chamber, and redirecting the clarified wastewater leaving the clarifier into a conduit comprising at least one valve, thereby producing a redirected clarified wastewater;
    (c) measuring the levels of total organic carbon and ammonia in the redirected clarified wastewater on an intermittent basis, and adding a source of phosphate ion, a source of ammonia, sodium hydroxide and an organic food source comprising at least one of acetic acid, ethyl acetate, molasses and mixtures thereof, to the redirected clarified wastewater to produce a minimal medium that is conveyed to the aeration chamber, wherein the minimal medium comprises an organic food source concentration that is between about 5 mM and about 20 mM, a phosphate ion concentration that is between about 500 uM and about 1 mM, an ammonia concentration that is between about 1 mM and about 2 mM and a pH that is between about pH 7.5 and about pH 9, and;
    (d) resuming the input of refinery wastewater to the aeration chamber after a period of time exceeding 1 week and discontinuing the redirecting of the clarified wastewater.

2. The process of claim 1, wherein the clarified wastewater is maintained with a dissolved oxygen content of at least 2 mg per liter.

3. The process of claim 1, wherein the clarified wastewater is maintained with a dissolved oxygen content of at least 5 mg per liter.

4. The process of claim 1, further comprising a step after step c) of intermittently removing a portion of the living culture to maintain an average living culture age of between 20 to 40 days.

5. The process of claim 4, wherein the removing of a portion of the activated sludge occurs daily.

6. The process of claim 4, wherein the removing of a portion of the activated sludge reduces the suspended solids to a concentration less than 4000 mg/L.

7. The process of claim 4, wherein the intermittently removing of a portion of the activated sludge reduces the suspended solids to a concentration less than 3000 mg/L.

8. The process of claim 1, wherein the period of time of part d) exceeds two weeks.

9. The process of claim 1, wherein the period of time of part d) exceeds four weeks.

10. The process of claim 1, wherein the measuring occurs daily.

11. The process of claim 1, wherein the refinery wastewater is derived from at least one of refinery desalter effluent, refinery stripped sour water, refinery tank bottom draws and spent caustic.

12. The process of claim 1, wherein the pH is maintained between about pH 8 and about pH 9.

* * * * *